(12) United States Patent
Jones

(10) Patent No.: US 6,305,591 B1
(45) Date of Patent: Oct. 23, 2001

(54) CONTAINER FOR AN ORTHODONTIC RETAINER

(76) Inventor: Janice M Jones, 977 Kingsbridge Dr., Rock Hill, SC (US) 29730

(*) Notice: Subject to any disclaimer, the term of this patent is extended or adjusted under 35 U.S.C. 154(b) by 0 days.

(21) Appl. No.: 09/412,409

(22) Filed: Oct. 5, 1999

Related U.S. Application Data

(60) Provisional application No. 60/103,102, filed on Oct. 5, 1998.

(51) Int. Cl.[7] .................................................. A45C 13/30
(52) U.S. Cl. ........................ 224/601; 224/604; 224/241; 224/269; 206/581; 206/63.5; 220/833; 220/839
(58) Field of Search ........................................ 224/576, 601, 224/602, 603, 604, 241, 269, 271; 206/581, 83, 63.5; 220/833, 839

(56) References Cited

U.S. PATENT DOCUMENTS

| | | | | |
|---|---|---|---|---|
| Re. 35,034 | * | 9/1995 | Albert | 206/63.5 |
| D. 50,842 | * | 5/1917 | McPhaden | 224/269 X |
| 3,567,085 | * | 3/1971 | Flores | 206/42 |
| 4,934,534 | * | 6/1990 | Wagner | 206/568 |
| 4,966,319 | * | 10/1990 | Fleming | 224/207 |
| 5,127,537 | * | 7/1992 | Graham | 220/339 |
| 5,312,029 | * | 5/1994 | Tuber | 224/252 |
| 5,388,739 | * | 2/1995 | Gargan | 224/202 |
| 5,743,449 | * | 4/1998 | McBride | 224/191 |
| 5,887,707 | * | 3/1999 | Anascavage | 206/63.5 |
| 5,967,305 | * | 10/1999 | Blonder et al. | 206/63.5 |

* cited by examiner

Primary Examiner—Stephen K. Cronin
(74) Attorney, Agent, or Firm—Michael A Mann; Nexsen Pruet Jacobs & Pollard LLC

(57) ABSTRACT

A container for holding an orthodontic retainer. The container comprises a front wall, an opposing back wall, a pair of opposing side walls, a bottom wall and a lid to define a cavity capable of holding an orthodontic retainer. The lid is hingedly attached to the back wall so the lid is not also easily lost. In a first preferred embodiment, a string is connected to the container that allows the user to hang the container from his neck. In a second preferred embodiment, a clip is formed in the back wall so that the user can attach the container to his clothing, much like an electronic pager.

12 Claims, 2 Drawing Sheets

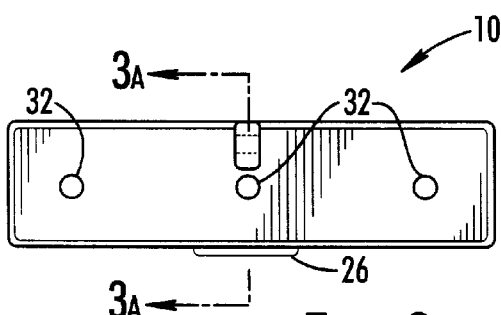
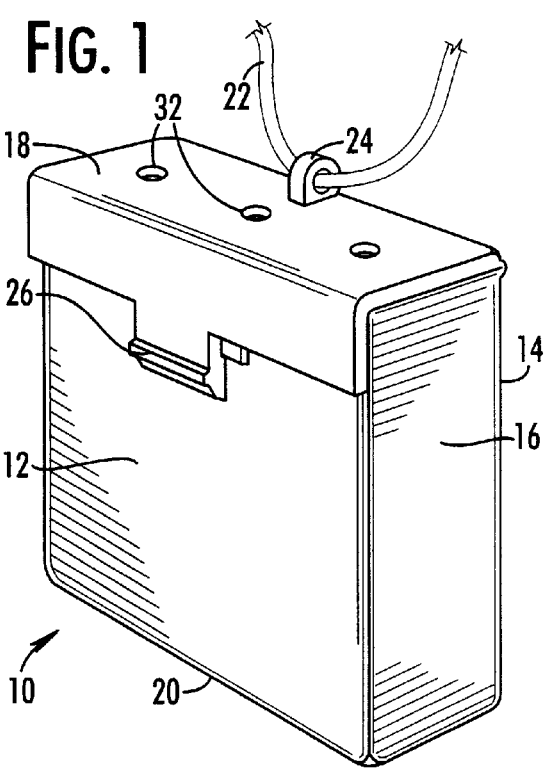
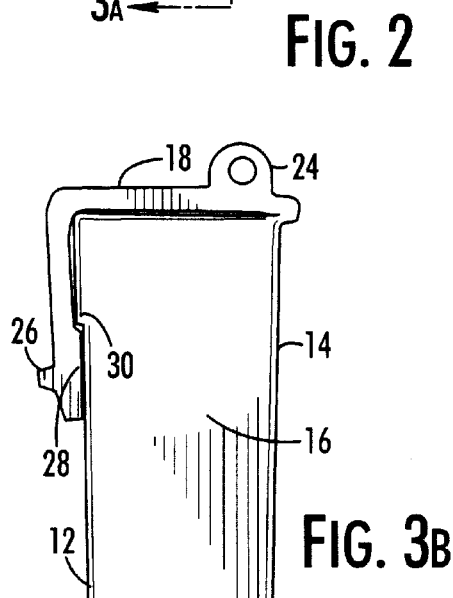
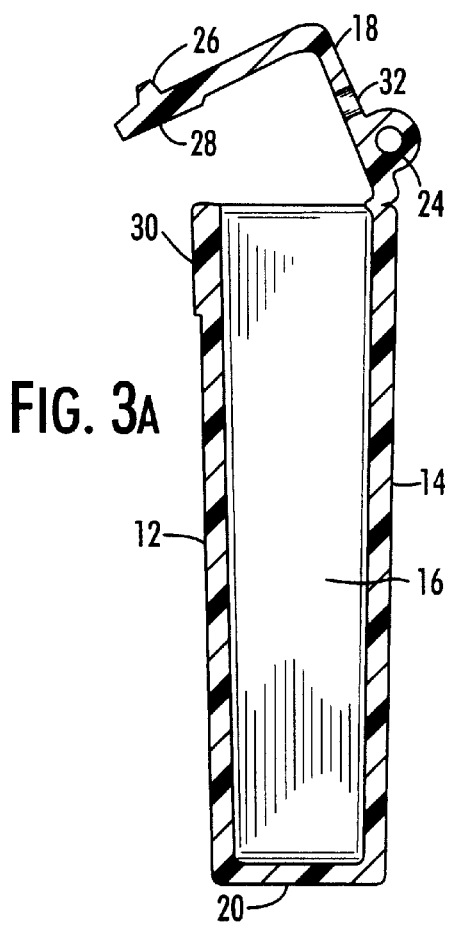

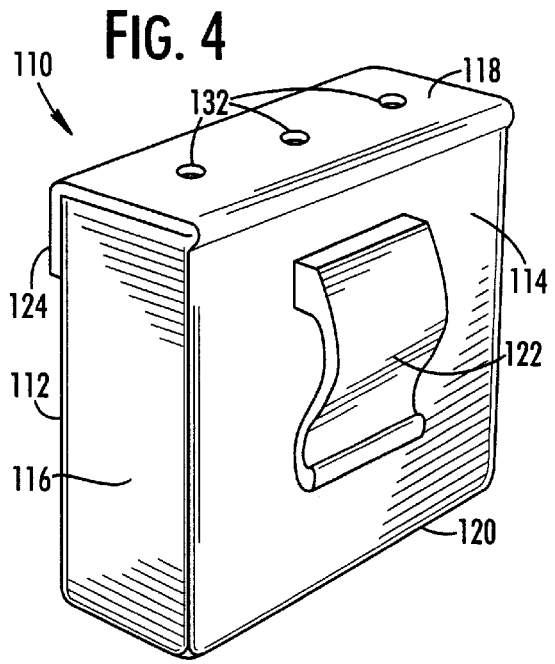
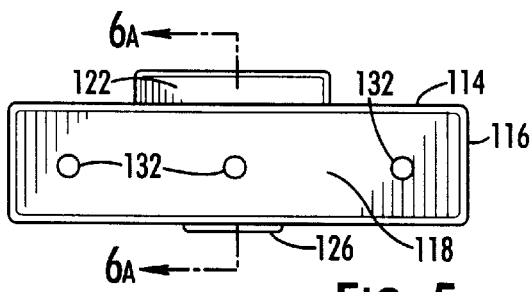
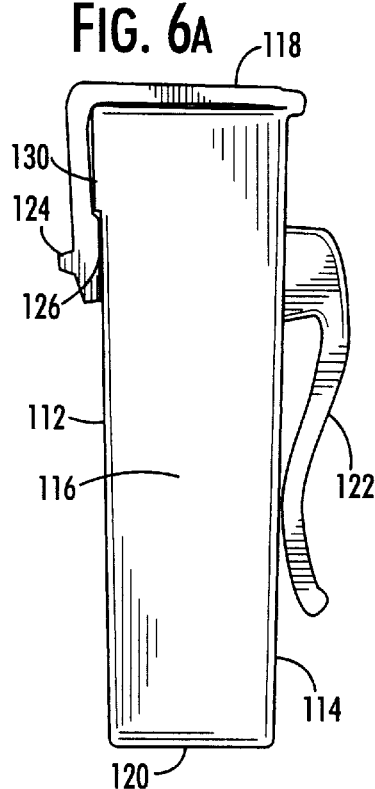
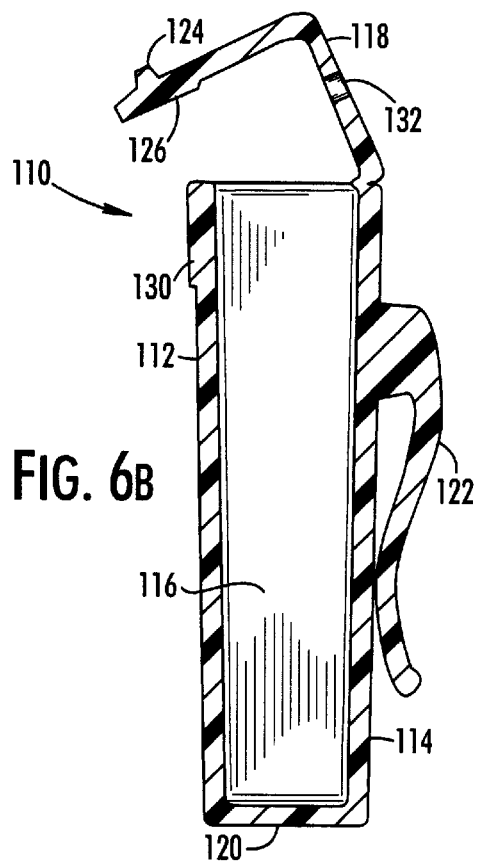

CONTAINER FOR AN ORTHODONTIC RETAINER

PRIORITY CLAIM

This application claims the benefit of U.S. Provisional Application No. 60/103,102, filed on Oct. 5, 1998.

BACKGROUND OF THE INVENTION

1. Field of the Invention

The present invention relates an article for holding a transportable orthodontic retainer.

2. Discussion of Background

Numerous people undergo months of orthodontic treatment to correct malocclusion. Although people of all ages wear braces, early treatment is generally advised. The American Association of Orthodontists recommends that children have a first visit with an orthodontist at age seven. The treatment typically comprises numerous adjustments performed over the course of 1–2 years at a cost of several thousand dollars.

Upon completion of the treatment, the braces are removed and a specially-designed retainer is used to prevent the teeth from shifting. Initially, the retainer must be worn at all times and should only be removed for special circumstances, such as meals, brushing, or active sports. The retainer may be used less frequently as the bite stabilizes.

Unfortunately, retainers are frequently forgotten and lost or damaged while not in use, such as at the cafeteria, restaurant, thrown in the trash, or athletic fields. Retainers are most often lost by younger wearers because of their higher levels of activity and lower attention span. Although retainers arrive in a container, the container is not convenient to carry about for short terms storage needs. Since insurance companies will not cover the cost of a lost retainer, each lost retainer adds expense. Therefore, there is a need for a way to prevent the loss of retainers when they are temporarily removed by the wearer.

SUMMARY OF THE INVENTION

According to its major aspects and broadly stated, the present invention is a container for holding an orthodontic retainer. The container comprises a front wall, an opposing back wall, a pair of opposing side walls, a bottom wall and a lid to define a cavity capable of holding an orthodontic retainer. The lid is hingedly attached to the back wall so the lid is not also easily lost. In the first preferred embodiment, a string is connected to the container to allow the user to hang the container from his neck. In the second preferred embodiment, a clip is formed in the back wall so that the user can attach the container to clothing, much like an electronic pager is attached.

The wearable container is a major feature of the present invention. When the retainer is not in use it is held in the container attached to (or hung from) the user. Thus, in the event the user forgets to reinsert the retainer in his mouth, the retainer is nonetheless not left behind.

A major advantage of the invention is the ability to easily carry the container from place to place. As a result, the user will be significantly less likely to lose his retainer. This advantage is implemented by different structural features in the two preferred embodiments. In a first embodiment, a string is connected to the container so the container may be hung from the user's neck; while a second embodiment has a clip formed in the back wall to allow attachment of the container to the user's clothing.

An important feature of the present invention is the use of a lid that is hingably attached to the container. Since the lid is permanently attached to the container, it can not be separately lost.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective view a container, according to a first preferred embodiment of the present invention;

FIG. 2 is a top view a container, according to a first preferred embodiment of the present invention;

FIG. 3A is a side cross-sectional view of a container in an open position, according to a first preferred embodiment of the present invention;

FIG. 3B is a side cross-sectional view a container in a closed position, according to a first preferred embodiment of the present invention;

FIG. 4 is a perspective view a container, according to a second preferred embodiment of the present invention;

FIG. 5 is a top view a container, according to a second preferred embodiment of the present invention;

FIG. 6A is a side cross-sectional view a container in an open position, according to a second preferred embodiment of the present invention;

FIG. 6B is a side cross-sectional view a container in a closed position, according to a second preferred embodiment of the present invention;

DETAILED DESCRIPTION OF A PREFERRED EMBODIMENT

Referring now to the figures, the present invention is a container for holding an article. Although the container could carry any article, the container is preferably used for holding an orthodontic retainer. An orthodontic retainer is a device that is inserted into the mouth of the user to retain the current positioning of teeth. The size of retainers vary depending upon the size of the user's mouth. A first preferred embodiment of a container, generally referred to by reference number 10, is illustrated in FIGS. 1–3 as having a string 22 that may be hung around the neck of the user. A second preferred embodiment of a container, generally referred to by reference number 110, is illustrated in FIGS. 4–6B as having a clip 122 capable of attachment to the user's clothing.

In a first preferred embodiment, container 10 comprises a front wall 12, an opposing back wall 14, a pair of opposing side walls 16, a bottom wall 20 and a lid 26 to define a cavity dimensioned for holding an orthodontic retainer. Walls 12, 14, 16, and 20 and lid 18 may have numerous sizes as long as the cavity defined by walls 12, 14, 16, and 20 is of sufficient dimension to hold an orthodontic retainer. Container 10 may be formed in the shape of any structure as long as the interior defines a cavity of sufficient dimensions to hold an orthodontic retainer. For lower manufacturing costs container 10 is preferably rectangular, but examples of various other shapes that conform generally to the shape of the retainer include but are not limited to disk-shaped, frusto-conical, and square. Although walls 12, 14, 16, and 20 may be formed from various materials, such as wood, aluminum, copper, stainless steel, fabric, leather, or any other like material, preferably walls 12, 14, 16, and 20 and lid 18 are formed from plastic.

Lid 18 is hingedly connected to back wall 14 so that lid 26 may be open as illustrated in FIG. 3A or closed as illustrated in FIG. 3B. Lid 18 has a lip 26 to seal container 10 so that clasp 28 can engage indentation 30 to securely fasten lid in a closed position. Although many different methods for securing lid in a closed position such as a button, zipper, hook and loop fasteners, or the like could be used, preferably clasp 28 engaging indentation 30 is used. A plurality of holes 32 are optionally positioned along lid 18 to provide ventilation for orthodontic retainer held in container 10.

A loop 24 having an opening for string 22 to go therethrough is positioned on lid. Preferably, a sufficient length of string 22 is used to form an opening that allows the user to hang container 10 from his neck using string 22; however, string may be secured to various other positions convenient to user, such as the user's belt, wrist, shirt.

In use, the lid 18 may be opened by pulling upward on lip 26 so that the orthodontic retainer may be placed inside container 10. The user then may close the lid 18 by pushing downward on lid 18 so that clasp 28 engages indentation 30. User may then hang container 10 around his neck or any other convenient position using string 22.

In a second preferred embodiment, container 110 comprises a front wall 112, an opposing back wall 114, a pair of opposing side walls 116, a bottom wall 120 and a lid 126 to define a cavity capable of holding an orthodontic retainer. Walls 112, 114, 116, and 120 and lid 118 may have numerous sizes as long as the cavity defined by walls 112, 114, 116, and 120 is of sufficient dimension to hold an orthodontic retainer. Container 110 may be formed in the shape of any structure that is capable of defining a cavity of sufficient dimensions to hold an orthodontic retainer. For lower manufacturing costs container 10 is preferably rectangular, but examples of various other shapes that generally conform to the shape of the retainer include but are not limited to disk-shaped, frusto-conical, and square. Although walls 112, 114, 116, and 120 may be formed from various materials, such as wood, aluminum, copper, stainless steel, fabric, leather, or any other like material, preferably walls 112, 114, 116, and 120 and lid 118 are formed from hard plastic.

Lid 118 is hingedly connected to back wall 114 so that lid 126 may be opened as illustrated in FIG. 6A or closed as illustrated in FIG. 6B. Lid 118 has a lip 126 to seal container 110 so that clasp 128 can engage indentation 30 to securely fasten lid 118 in a closed position. Although many different methods for securing lid 118 in a closed position such as a button, zipper, hook and loop fasteners, or the like could be used, preferably clasp 128 engaging indentation 130 is used. A plurality of holes 132 are optionally positioned along lid 118 to provide ventilation for orthodontic retainer held in container 10.

A clip 122 is preferably formed on back wall 114 to allow user to attach container 110 to his clothing. Clip 122 functions similarly to an electronic pager clip, with a sufficient spring action to allow the user to fasten container to clothing.

In use, lid 118 may be opened by pulling upward on lip 126 so that the orthodontic retainer may be placed inside container 10. The user then may close the lid 118 by pushing downward on lid 118 so that clasp 128 engages indentation 130 The user may attach container to clothing by fastening clip to belt, shirt, pants, or the like.

It will be apparent to those skilled in the art that many changes and substitutions can be made to the preferred embodiment herein described without departing from the spirit and scope of the present invention.

What is claimed is:

1. A container for use with an orthodontic retainer, said container comprising:

an orthodontic retainer;

a housing having a cavity of sufficient dimensions to receive said orthodontic retainer, said housing having an opening that allows access to said cavity;

a lid removably secured to said housing, said lid covering said opening and having a plurality of holes; and a string attached to said lid.

2. The container as recited in claim 1, wherein said lid is hingedly secured to said housing.

3. The container as recited in claim 1, wherein said lid has means for locking said lid to said housing.

4. The container as recited in claim 1, wherein said housing is formed from plastic.

5. A container for use with an orthodontic retainer, said container comprising, an orthodontic retainer;

a housing having a cavity of sufficient dimension to receive said orthodontic retainer, said housing having an opening that allows access to said cavity;

a lid removably secured to said housing, said lid covering said opening and having a plurality of holes; and a clip integrally formed in said housing.

6. The container as recited in claim 5, wherein said lid is hingedly secured to said housing.

7. The container as recited in claim 5, wherein said lid has locking means for locking said lid to said housing.

8. The container as recited in claim 5, wherein said housing is formed from plastic.

9. A container for use with an orthodontic retainer, said container comprising:

an orthodontic retainer;

a housing having a cavity of sufficient dimension to receive said orthodontic retainer, said housing having an opening that allows access to said cavity;

a lid removably secured to said housing, said lid covering said opening and having a plurality of holes; and a clip integrally formed in said housing.

10. The container as recited in claim 9, wherein said lid is hingedly secured to said housing.

11. The container as recited in claim 9, herein said lid has locking means for locking said lid to said housing.

12. The container as recited in claim 9, wherein said housing is formed from plastic.

* * * * *